(12) United States Patent
Prokop et al.

(10) Patent No.: US 12,324,768 B2
(45) Date of Patent: Jun. 10, 2025

(54) DEVICES, SYSTEMS, AND METHODS FOR PRE-HEATING FLUID TO BE INTRODUCED INTO A PATIENT DURING A SURGICAL PROCEDURE

(71) Applicant: Covidien LP, Mansfield, MA (US)

(72) Inventors: Paul F. Prokop, Woburn, MA (US); Jordan A. Whisler, Brookline, MA (US); Dale E. Whipple, Nashua, NH (US)

(73) Assignee: Covidien LP, Mansfield, MA (US)

( * ) Notice: Subject to any disclaimer, the term of this patent is extended or adjusted under 35 U.S.C. 154(b) by 1025 days.

(21) Appl. No.: 17/353,379

(22) Filed: Jun. 21, 2021

(65) Prior Publication Data

US 2021/0307958 A1   Oct. 7, 2021

Related U.S. Application Data

(63) Continuation of application No. 16/163,830, filed on Oct. 18, 2018, now Pat. No. 11,065,147.

(51) Int. Cl.
| | | |
|---|---|---|
| *A61F 7/00* | (2006.01) | |
| *A61B 18/14* | (2006.01) | |
| *A61B 18/00* | (2006.01) | |
| *A61B 18/04* | (2006.01) | |

(52) U.S. Cl.
CPC ........ *A61F 7/0085* (2013.01); *A61B 18/1445* (2013.01); *A61B 2018/00005* (2013.01); *A61B 2018/046* (2013.01); *A61M 2210/1433* (2013.01)

(58) Field of Classification Search
CPC ... A61B 18/04; A61B 2018/044; A61B 17/32; A61B 17/320016; A61B 18/1445; A61B 2018/046; A61B 17/32002; A61B 2018/00005; A61B 2217/005; A61B 2217/007; A61F 7/00; A61F 7/0088; A61F 7/007; A61F 7/0085; A61F 2007/0059; A61M 2210/1433
See application file for complete search history.

(56) References Cited

U.S. PATENT DOCUMENTS

| | | | |
|---|---|---|---|
| 1,585,934 | A | 5/1926 | Muir |
| 1,666,332 | A | 4/1928 | Hirsch |
| 1,831,786 | A | 11/1931 | Duncan |
| 2,708,437 | A | 5/1955 | Hutchins |
| 3,297,022 | A | 1/1967 | Wallace |
| 3,686,706 | A | 8/1972 | Finley |

(Continued)

*Primary Examiner* — Jason E Flick
(74) *Attorney, Agent, or Firm* — Carter, DeLuca & Farrell LLP

(57) ABSTRACT

A surgical system includes a fluid source including a fluid inflow tube, a fluid delivery device coupled to the fluid inflow tube and configured to deliver fluid from the fluid source into a patient, a surgical instrument, and a control box coupled to the surgical instrument. The control box includes one or more waste heat-generating electronic components and a heat pipe assembly disposed in thermal communication with the one or more waste heat-generating electronic components. The fluid inflow tube is disposed in thermal communication with the heat pipe assembly of the control box such that the heat pipe assembly conducts heat away from the one or more waste heat-generating electronic components and heats fluid flowing through the fluid inflow tube.

22 Claims, 3 Drawing Sheets

(56) References Cited

U.S. PATENT DOCUMENTS

| | | |
|---|---|---|
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,971,034 A | 11/1990 | Poi et al. |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,586,973 A | 12/1996 | Lemaire et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |

(56) References Cited

U.S. PATENT DOCUMENTS

| | | |
|---|---|---|
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,025,656 B2 | 9/2011 | Gruber et al. |
| 8,061,359 B2 | 11/2011 | Emanuel |
| 8,062,214 B2 | 11/2011 | Shener et al. |
| 8,419,626 B2 | 4/2013 | Shener-Irmakoglu et al. |
| 8,465,421 B2 | 6/2013 | Finkman et al. |
| 8,523,852 B2 * | 9/2013 | Manwaring ........ A61B 18/1492 607/47 |
| 8,528,563 B2 | 9/2013 | Gruber |
| 8,574,253 B2 | 11/2013 | Gruber et al. |
| 8,617,151 B2 * | 12/2013 | Denis .................... A61B 18/10 606/31 |
| 8,647,349 B2 | 2/2014 | Gruber et al. |
| 8,663,264 B2 | 3/2014 | Cesarini et al. |
| 8,678,999 B2 | 3/2014 | Isaacson |
| 8,834,487 B2 | 9/2014 | Gruber et al. |
| 8,840,625 B2 | 9/2014 | Adams et al. |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,760 B2 | 6/2015 | Sullivan et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,095,366 B2 | 8/2015 | Sullivan et al. |
| 9,125,550 B2 | 9/2015 | Shener-Irmakoglu et al. |
| 9,155,454 B2 | 10/2015 | Sahney et al. |
| 9,259,233 B2 | 2/2016 | Gruber et al. |
| 11,065,147 B2 | 7/2021 | Prokop et al. |
| 2001/0039963 A1 | 11/2001 | Spear et al. |
| 2001/0047183 A1 | 11/2001 | Privitera et al. |
| 2002/0058859 A1 | 5/2002 | Brommersma |
| 2002/0165427 A1 | 11/2002 | Yachia et al. |
| 2003/0050603 A1 | 3/2003 | Todd |
| 2003/0050638 A1 | 3/2003 | Yachia et al. |
| 2003/0078609 A1 | 4/2003 | Finlay et al. |
| 2003/0114875 A1 | 6/2003 | Sjostrom |
| 2004/0204671 A1 | 10/2004 | Stubbs et al. |
| 2005/0043690 A1 | 2/2005 | Todd |
| 2005/0085692 A1 | 4/2005 | Kiehn et al. |
| 2006/0036132 A1 | 2/2006 | Renner et al. |
| 2006/0047185 A1 | 3/2006 | Shener |
| 2006/0241586 A1 | 10/2006 | Wilk |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0270812 A1 | 10/2009 | Litscher et al. |
| 2009/0270895 A1 | 10/2009 | Churchill |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0152647 A1 | 6/2010 | Shener et al. |
| 2011/0034943 A1 | 2/2011 | Churchill et al. |
| 2011/0077674 A1 | 3/2011 | Sullivan et al. |
| 2011/0118544 A1 | 5/2011 | Adams et al. |
| 2011/0166419 A1 | 7/2011 | Reif et al. |
| 2012/0067352 A1 | 3/2012 | Gruber et al. |
| 2012/0078038 A1 | 3/2012 | Sahney et al. |
| 2013/0131452 A1 | 5/2013 | Kuroda et al. |
| 2014/0031834 A1 | 1/2014 | Germain et al. |
| 2015/0051598 A1 * | 2/2015 | Orszulak ............ A61B 18/1445 606/39 |
| 2017/0143930 A1 * | 5/2017 | Noah ................ A61M 16/1095 |

* cited by examiner

DEVICES, SYSTEMS, AND METHODS FOR PRE-HEATING FLUID TO BE INTRODUCED INTO A PATIENT DURING A SURGICAL PROCEDURE

CROSS-REFERENCE TO RELATED APPLICATIONS

This application is a continuation of U.S. patent application Ser. No. 16/163,830, filed on Oct. 18, 2018, the entire contents of which are hereby incorporated herein by reference.

BACKGROUND

1. Technical Field

The present disclosure relates generally to surgical devices, surgical systems and surgical methods utilizing fluid introduced into a patient. More particularly, the present disclosure relates devices, systems, and methods for pre-heating fluid to be introduced into a patient during a surgical procedure.

2. Background of Related Art

Surgical procedures, such as tissue resection procedures, may be performed endoscopically within an organ, such as a uterus, by inserting an endoscope into the uterus and passing a tissue resection device through the endoscope and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space. The inflow fluid may be provided from a fluid bag, or other fluid source, and is typically maintained at room temperature.

In some surgical procedures, it may be desirable to pre-heat the fluid introduced into the patient. Pre-heating the fluid may be advantageous, for example, in order to make the introduction of fluid into the patient more palatable by reducing or eliminating the temperature differential between the fluid and the patient.

SUMMARY

As used herein, the term "distal" refers to the portion that is described which is further from a user, while the term "proximal" refers to the portion that is described which is closer to a user. Further, to the extent consistent, any or all of the aspects described herein may be used in conjunction with any or all of the other aspects described herein.

Provided in accordance with aspects of the present disclosure is a surgical system including a fluid source including a fluid inflow tube, a fluid delivery device coupled to the fluid inflow tube and configured to deliver fluid from the fluid source into a patient, a surgical instrument, and a control box coupled to the surgical instrument. The control box includes one or more waste heat-generating electronic components and a heat pipe assembly disposed in thermal communication with the one or more waste heat-generating electronic components. The fluid inflow tube is disposed in thermal communication with the heat pipe assembly of the control box such that the heat pipe assembly conducts heat away from the one or more waste heat-generating electronic components and heats fluid flowing through the fluid inflow tube.

In an aspect of the present disclosure, the heat pipe assembly includes at least one heat pipe.

In another aspect of the present disclosure, the control box further includes an outer housing enclosing the one or more waste heat-generating electronic components therein. In such aspects, the heat pipe assembly includes at least one internal heat pipe disposed within the outer housing and at least one external heat pipe disposed at least partially externally of the outer housing.

In another aspect of the present disclosure, the heat pipe assembly includes at least one heat pipe and a tube-receiving sleeve configured to receive a portion of the fluid inflow tube therein. The tube-receiving sleeve is disposed in thermal communication with the at least one heat pipe and the at least one heat pipe is disposed in thermal communication with one or more of the waste heat-generating electronic components.

In still another aspect of the present disclosure, the heat pipe assembly further includes at least one panel. Each panel is disposed in thermal communication with at least one of the heat pipes.

In yet another aspect of the present disclosure, a portion of the heat pipe assembly directly contacts one or more of the waste heat-generating electronic components.

In still yet another aspect of the present disclosure, the one or more waste heat-generating electronic components includes some or all of: a touch-screen display assembly, a motor control assembly, a power supply, a vacuum pump assembly, an identification assembly, or a fluid monitoring assembly.

In another aspect of the present disclosure, the fluid source is a fluid bag retaining fluid therein.

In another aspect of the present disclosure, the fluid delivery device is an endoscope.

In still another aspect of the present disclosure, the surgical instrument is a tissue resecting instrument.

A control box provided in accordance with aspects of the present disclosure and configured to couple to a surgical instrument to facilitate operation of the surgical instrument includes an outer housing, one or more waste heat-generating electronic components configured to facilitate operation of a surgical instrument, and a heat pipe assembly. The one or more waste heat-generating electronic components is disposed within the outer housing. The heat pipe assembly includes at least one internal heat pipe disposed within the outer housing, at least one external heat pipe disposed at least partially outside the outer housing, and a tube-receiving sleeve disposed outside the outer housing. The internal heat pipe(s), the external heat pipe(s), and the tube-receiving sleeve are disposed in thermal communication with the one or more waste heat-generating electronic components and configured to conduct waste heat from the one or more waste heat-generating electronic components to a fluid tube disposed within the tube-receiving sleeve to heat fluid flowing through the tube-receiving sleeve.

In an aspect of the present disclosure, the heat pipe assembly further includes at least one panel disposed within the outer housing. Each panel is disposed in thermal communication with one or more of the internal heat pipes.

In another aspect of the present disclosure, at least one of the internal heat pipes directly contacts at least one of the waste heat-generating electronic components.

In still another aspect of the present disclosure, the one or more waste heat-generating electronic components includes some or all of: a touch-screen display assembly, a motor control assembly, a power supply, a vacuum pump assembly, an identification assembly, or a fluid monitoring assembly.

In yet another aspect of the present disclosure, the tube-receiving sleeve defines a C-shaped cross-sectional configuration.

BRIEF DESCRIPTION OF THE DRAWINGS

Various aspects and features of the present disclosure are described hereinbelow with reference to the drawings wherein like numerals designate identical or corresponding elements in each of the several views and.

DETAILED DESCRIPTION

Figure 1:
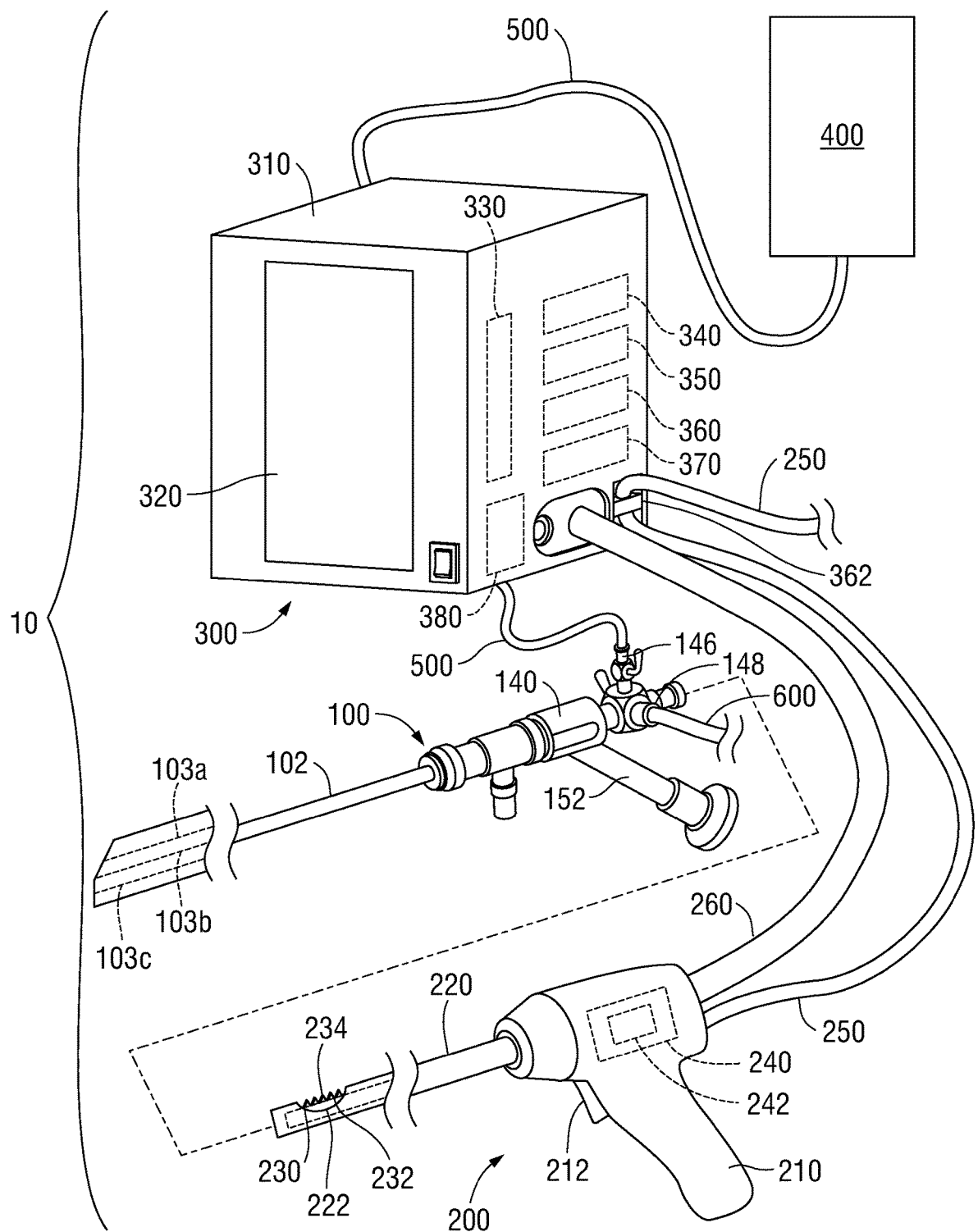
FIG. 1 is a front, perspective view of a surgical system provided in accordance with aspects of the present disclosure including an endoscope (wherein the distal portion thereof is enlarged for illustration purposes), a surgical instrument, a control box, and a fluid source including an inflow fluid tube.

Referring to FIG. 1 a surgical system exemplifying the aspects and features of the present disclosure is shown generally identified by reference numeral 10. Surgical system 10 generally includes an endoscope 100, a surgical instrument 200, a control box 300, and a fluid source 400 including an inflow fluid tube 500. Although detailed herein with respect to surgical system 10, the aspects and features of the present disclosure are equally applicable for use with other surgical systems. For the purposes herein, the components of surgical system 10 are generally described.

Endoscope 100 of surgical system 10 is detailed herein as a hysteroscope configured for use in gynecological surgical procedures within the uterus. However, other suitable endoscopes and fluid-delivery devices are also contemplated. Endoscope 100 includes an elongated tubular member 102 and a proximal body 140. Proximal body 140 includes an inflow valve 146, an outflow valve 148, and an arm 152 that is configured to connect to an imaging device (e.g., a camera) to capture images received via a visualization mechanism, e.g., optics (not shown), extending through elongated tubular member 102.

Elongated tubular member 102 of endoscope 100 defines a first channel 103a for fluid inflow, a second channel 103b that is shared between fluid outflow and instrument access, e.g., for instrument 200, and a third channel 103c housing optics (not shown). First channel 103a is coupled to inflow valve 146 to enable the introduction of fluid through first channel 103a of endoscope 100 and into a patient, e.g., into a patient's uterus. Fluid inflow fluid tube 500 of fluid source 400 is coupled to inflow valve 146 for enabling the delivery of fluid from fluid source 400 to endoscope 100 and, thus, from fluid source 400 into the patient. Second channel 103b is coupled to outflow valve 148 via an outflow fluid tube 600 to enable the withdrawal of fluid from the patient through endoscope 100 and outflow fluid tube 600, e.g., for depositing in one or more collection canisters (not shown) coupled to outflow fluid tube 600.

Continuing with reference to FIG. 1, surgical instrument 200 is detailed herein as a tissue resecting instrument; however other suitable surgical instruments are also contemplated. Surgical instrument 200 generally includes a housing 210, a shaft 220, a cutting member 230, a drive mechanism 240, an outflow tissue and fluid tubing 250, and a cable 260. Housing 210 houses drive mechanism 240 therein and functions as a handle to enable a user to grasp and manipulate surgical instrument 200. Housing 210 may include an actuator 212 disposed thereon for selectively activating surgical instrument 200.

Shaft 220 extends distally from housing 210 and, in embodiments, is stationary relative to housing 210, although other configurations are also contemplated. Shaft 220 defines a window 222 through a side wall thereof towards a distal end thereof to provide access to cutting member 230 which is rotatably and/or translatably disposed within shaft 220 and operably coupled to drive mechanism 240, as detailed below. Cutting member 230 defines an opening 232 providing access to the interior thereof and may include a serrated cutting edge 234 surrounding opening 232, although other suitable cutting edge configurations are also contemplated. Alternatively or additionally, shaft 220 may include a cutting edge defined about window 222.

Drive mechanism 240 includes a motor 242 and is operably coupled to cutting member 230 to drive rotation and/or translation of cutting member 230 relative to shaft 220. Drive mechanism 240 is adapted to connect to control box 300 via cable 260 for powering and controlling motor 242. Actuator 212 may be coupled to drive mechanism 240 and/or control box 300 to enable the selective activation of surgical instrument 200, e.g., selective rotation and/or translation of cutting member 230.

Outflow tissue and fluid tubing 250 receives the resected tissue as well as fluid and debris suctioned through cutting member 230 when surgical instrument 200 is activated. Outflow tissue and fluid tubing 250 is operably coupled with a vacuum pump assembly 360 of control box 300, e.g., via tubing interface 362, to enable the suctioning of the resected tissue, fluid, and debris through cutting member 230 and into outflow tissue and fluid tubing 250 for depositing within one or more collection canisters (not shown) coupled with tissue and fluid tubing 250.

With continued reference to FIG. 1, control box 300, as noted above, is configured to power and control motor 242 of drive mechanism 240 of surgical instrument 200 and to provide suction, via vacuum pump assembly 360 (although other suitable suction sources are also contemplated), to suction resected tissue, fluid, and debris through surgical instrument 200 and outflow tissue and fluid tubing 250 for depositing in one or more of the collection canisters (not shown). Control box 300 may additionally or alternatively include communication, identification, and parameter monitoring components, as detailed below.

Control box 300 generally includes an outer housing 310, a touch-screen display 320 accessible from the exterior of outer housing 310, a touch-screen display assembly 330 disposed within outer housing 310 and configured to control the display of information on touch-screen display 320 and sense information input thereto, a motor control assembly 340 disposed within outer housing 310 and configured to control drive mechanism 240 of surgical instrument 200, a power supply 350 disposed within outer housing 310 and configured to convert power from a mains power supply (not shown) into suitable form for powering drive mechanism 240 of surgical instrument 200, and a vacuum pump assembly 360 configured to suction and control the suctioning of resected tissue, fluid, and debris through surgical instrument 200.

Control box 300 may further include an identification (ID) assembly 370 configured to identify a surgical instrument, e.g., surgical instrument 200, coupled thereto, e.g., via RFID. Control box 300 may additionally or alternatively include a fluid monitoring assembly 380 configured to, for example, monitor fluid flow rate, fluid pressure, total fluid volume, fluid impedance, fluid deficit, etc., and provide feedback regarding the same, e.g., suitable alarms and/or disabling of one or more other assemblies. Control box 300 further includes an output 390 enabling coupling of cable 260 of surgical instrument 200 to control box 300. Additional or alternative assemblies and/or other components associated with control box 300 may also be provided.

As can be appreciated in view of the above, the various assemblies 330-380 of control box 300 include suitable hardware components and may also include one or more processors and associated memories storing software to be executed by the processor(s) to control the hardware components (although one or more centralized processors and/or memories may alternatively be provided). These assemblies 330-380, as with all such electronic components, generate waste heat during use. Currently, control boxes dissipate waste heat by use of an exhaust fan, venting, and/or one or more heat sinks so as to maintain the electronic components at safe operating temperatures.

Figure 2:
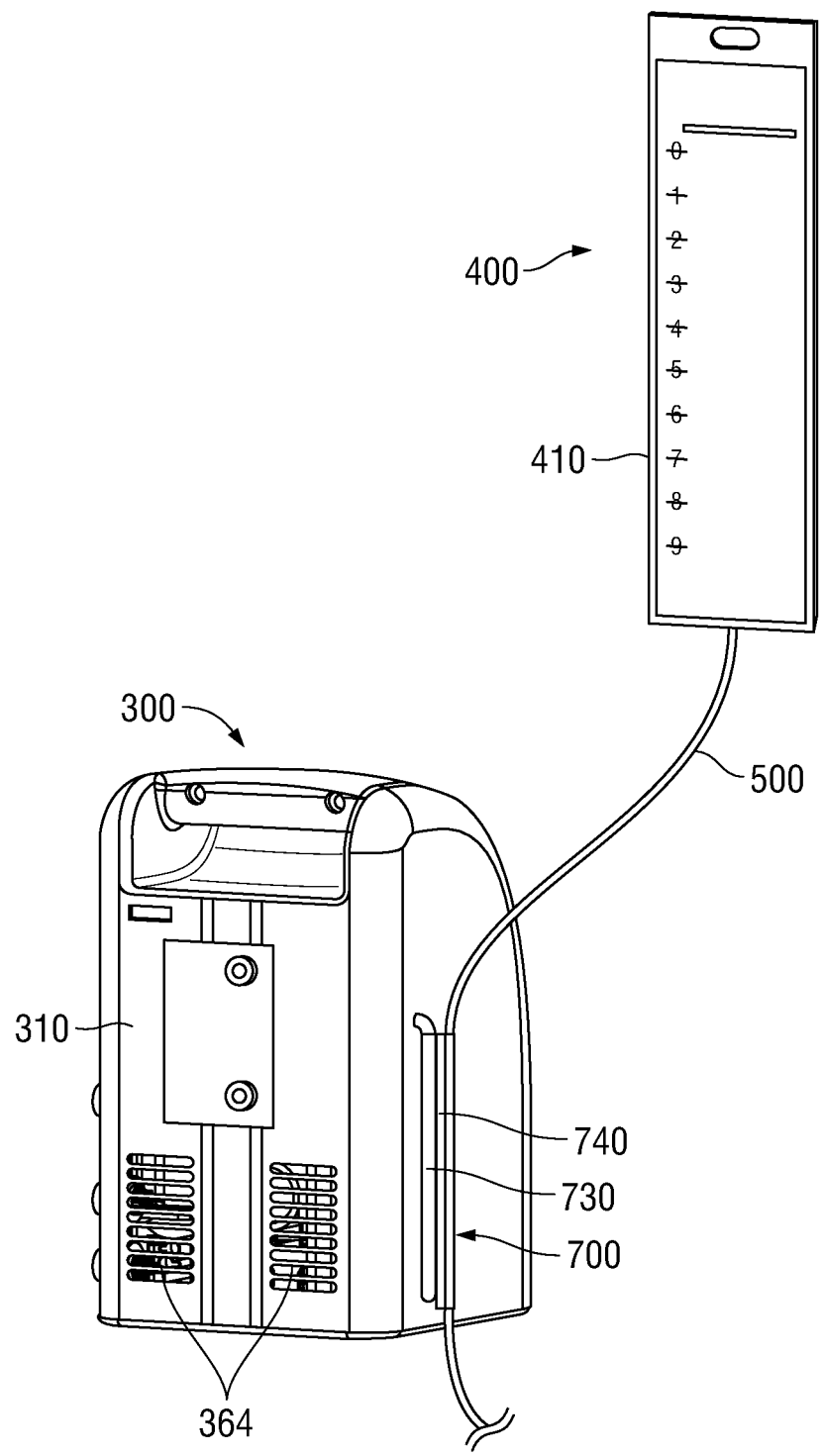
FIG. 2 is a rear, perspective view of the control box and fluid source of the surgical system of FIG. 1 with the inflow fluid tube of the fluid source thermally coupled to the control box.
Figure 3:
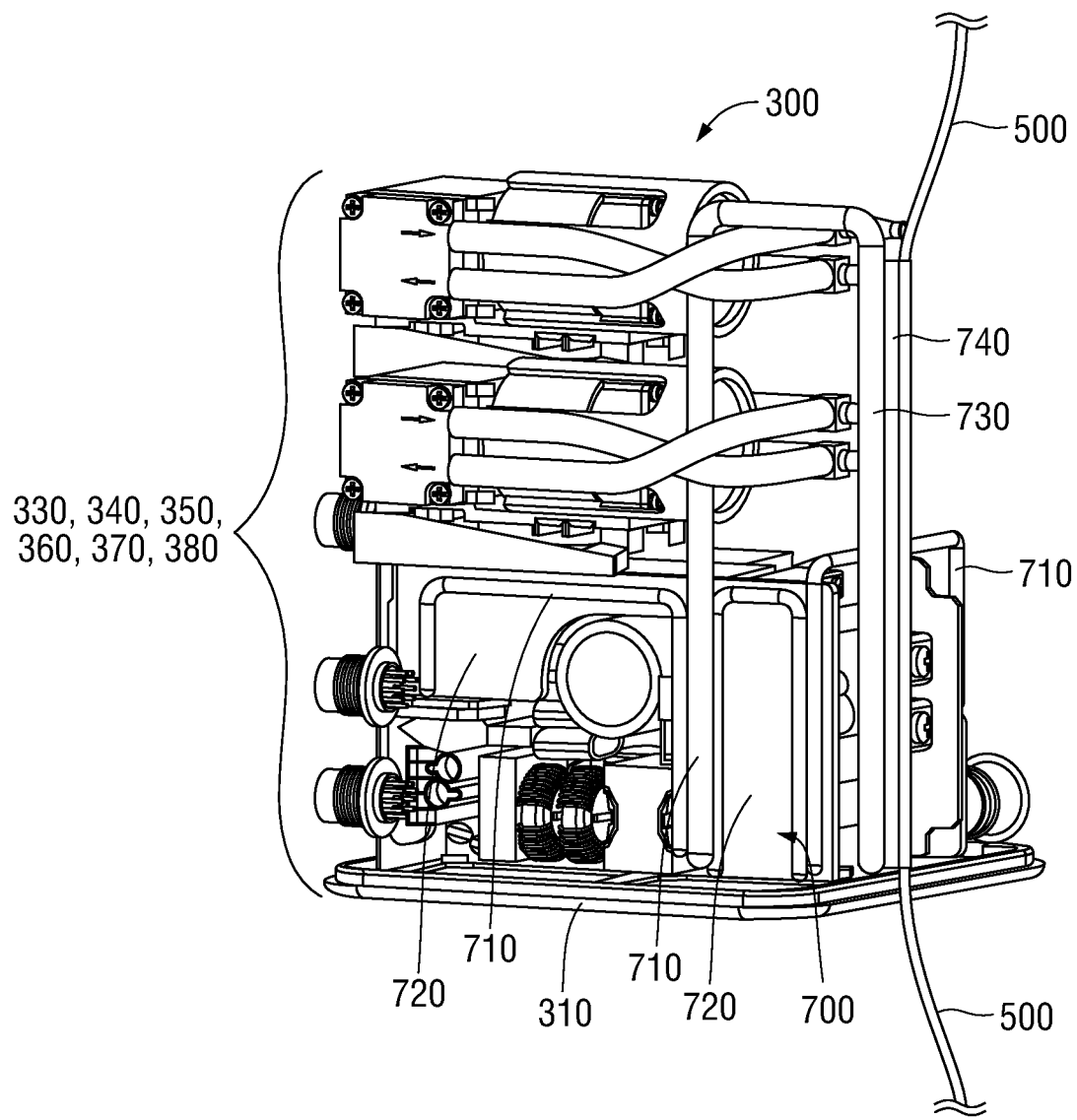
FIG. 3 is a perspective view of the control box and the inflow fluid tube of the fluid source of the surgical system of FIG. 1 with an outer housing of the control box removed to illustrate the internal components of the control box thermally coupled to the inflow fluid tube.

With additional reference to FIGS. 2 and 3, control box 300 of the present disclosure includes a heat pipe assembly 700 integrated therewith that harnesses the waste heat produced by the electronic components, e.g., assemblies 330-380, for use in pre-heating the fluid flowing through inflow fluid tube 500 (from fluid source 400). Heat pipe assembly 700 generally includes a plurality of internal heat pipes 710 disposed within outer housing 310 of control box 300 and formed from a thermally-conductive material, e.g., a metal, and a plurality of internal panels 720 disposed within outer housing 310 and formed from a thermally-conductive material, e.g., a metal. Internal heat pipes 710 may include water or any other suitable heat-transfer fluid therein. Internal heat pipes 710 and internal panels 720 disposed in thermal communication, e.g., direct contact, contact through another thermally-conductive material, and/or close approximation, with one another. Internal heat pipes 710 and internal panels 720 are disposed adjacent one or more of the waste heat-generating electronic components of assemblies 330-380, through one or more of the waste heat-generating electronic components, and/or between two or more of the waste heat-generating electronic components in thermal communication therewith (via direct contact, indirect contact, or close approximation). In this manner, internal heat pipes 710 and internal panels 720 conduct and withdraw the waste heat generated by the waste heat-generating electronic components of some or all of assemblies 330-380.

Continuing with reference to FIGS. 1-3, heat pipe assembly 700 further includes one or more external heat pipes 730 (one (1) external heat pipe 730 is illustrated in FIGS. 2 and 3) extending through outer housing 310 and along at least a portion of the exterior surface thereof. External heat pipe 730 is disposed in thermal communication (via direct contact, indirect contact, or close approximation) with internal heat pipes 710 and internal panels 720. External heat pipe 730 may include water or any other suitable heat-transfer fluid therein and is formed from a thermally-conductive material, e.g., a metal. One or more of the internal heat pipes 710 may be fluidly coupled with one another and/or fluidly coupled with external heat pipe 730.

Heat pipe assembly 700 additionally includes a tube-receiving sleeve 740 disposed externally of outer housing 310, in thermal communication, e.g., direct contact, indirect contact, and/or close approximation, with external heat pipe 730, and extending along at least a portion of the length of external heat pipe 730. Tube-receiving sleeve 740 is formed from a thermally-conductive material, e.g., a metal, defines a C-shaped cross-sectional configuration (although other configurations are also contemplated), and is configured to receive a portion of fluid inflow tube 500 therein, e.g., via passage through the mouth defined by the C-shaped cross-sectional configuration of tube-receiving sleeve 740.

As noted above, internal heat pipes 710 and internal panels 720 conduct and withdraw the waste heat generated by the waste heat-generating electronic components of assemblies 330-380. More specifically, the conduction of the waste heat by internal heat pipes 710 and internal panels 720 heats the nearby liquid fluid, e.g., water, within internal heat pipes 710 to a vapor state. The vapor then travels through the internal heat pipe(s) 710 away from the waste heat source(s) to, for example, external heat pipe 730, wherein, with the vapor sufficiently removed from the heat source(s), the vapor is condensed back into a liquid state, releasing heat that is conducted by external heat pipe 730 and tube-receiving sleeve 740, which is disposed in thermal communication with external heat pipe 730. This heating of tube-receiving sleeve 740, in turn, heats a tube engaged therein, e.g., fluid inflow tube 500, and, thus, the fluid flowing through fluid inflow tube 500. In addition to heating the fluid flowing through fluid inflow tube 500, heat pipe assembly 700 also serves as a cooling device for assemblies 330-380 by conducting heat away from assemblies 330-380, as detailed above. Internal panels 720 define relatively large surface areas to facilitate the conduction of waste heat from assemblies 330-380 to internal heat pipes 710.

Referring back to FIGS. 1 and 2, fluid source 400 may be, for example, a fluid bag 410 containing a fluid, e.g., saline, sorbitol, or glycine, therein. Fluid bag 410 is connected to an input end of fluid inflow tube 500 which, as noted above, is coupled at an output end thereof to inflow valve 146 for enabling delivery of fluid from fluid source 400 to endoscope 100. A length of fluid inflow tube 500, as illustrated in FIGS. 2 and 3, is disposed within tube-receiving sleeve 740 of heat pipe assembly 700 such that fluid flowing from fluid bag 410 to endoscope 100 is heated via heat pipe assembly 700 as it flows through the portion of fluid inflow tube 500 disposed within tube-receiving sleeve 740 of heat pipe assembly 700. Fluid source 400 delivers fluid to endoscope 100 under gravity pressure. In other embodiments, a pressure pump or other suitable pump (not shown) may be provided to communicate with fluid inflow tube 500 (upstream or downstream of heat pipe assembly 700) or may be associated with fluid source 400 to pressurize the fluid supplied to endoscope 100.

With reference to FIGS. 1-3, as noted above, control box 300 may include vacuum pump assembly 360 to suction resected tissue, fluid, and debris through surgical instrument 200. Vacuum pump assembly 360 may include any suitable vacuum pump having an exhaust to expel waste air therefrom. Typically, this waste air is expelled from the outer housing via vents 364 (FIG. 2). However, in embodiments of the present disclosure, the exhausted waste air from vacuum pump assembly 360 may be directed towards, over/under, between, through, etc. some or all of assemblies 330-380 such that the waste air is utilized to help cool assemblies 330-380. This repurposing of the waste air eliminates the need for a cooling fan or fans, reduces the number of cooling fans, and/or reduces the required output of the cooling fan(s). Additionally, an exhaust augmentor (not shown) operably coupled to the exhaust outflow of vacuum pump assembly 360 may be provided to draw in external air, e.g., through vents 364, to supplement the waste air, thereby further facilitating cooling of assemblies 330-380. The above-detailed waste air repurposing may be provided in conjunction with heat pipe assembly 700 or may be provided in systems that do not include heat pipe assembly 700.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A surgical system, comprising:
a control box, including:
an outer housing;
at least one waste heat-generating electronic component disposed within the outer housing;
at least one heat pipe disposed within the outer housing or along an exterior of the outer housing; and
a tube-receiving sleeve disposed exteriorly of the outer housing, the at least one heat pipe disposed in thermal communication with the tube-receiving sleeve and the at least one waste heat-generating electronic component and configured to conduct waste heat from the at least one waste heat-generating electronic component to a fluid tube disposed within the tube-receiving sleeve to heat fluid flowing through the fluid tube.

2. The surgical system according to claim 1, further comprising:
a fluid source configured to supply fluid to the fluid tube; and
a fluid delivery device configured to receive the fluid from the fluid tube, wherein a temperature of the fluid at the fluid delivery device is greater than a temperature of the fluid at the fluid source.

3. The surgical system according to claim 2, wherein the fluid delivery device is an endoscope.

4. The surgical system according to claim 3, wherein the fluid delivery device is a hysteroscope.

5. The surgical system according to claim 1, wherein at least one of the at least one heat pipes directly contacts at least one of the at least one waste heat-generating electronic components.

6. The surgical system according to claim 1, wherein one of the at least one heat pipes is disposed within the outer housing and wherein another of the at least one heat pipes is disposed along the exterior of the outer housing.

7. The surgical system according to claim 6, wherein the at least one waste heat-generating electronic component includes at least one of: a touch-screen display assembly, a motor control assembly, a power supply, a fluid pump assembly, an identification assembly, or a fluid monitoring assembly.

8. The surgical system according to claim 1, wherein the tube-receiving sleeve defines a C-shaped cross-sectional configuration.

9. A surgical system, comprising:
a control box, including:
an outer housing;
at least one waste heat-generating electronic component disposed within the outer housing;
a heat exchanger disposed in thermal communication with the at least one waste heat-generating electronic component; and
a tube-receiving sleeve disposed exteriorly of the outer housing, the tube-receiving sleeve disposed in thermal communication with the heat exchanger, wherein the heat exchanger is configured to conduct waste heat from the at least one waste heat-generating electronic component to a fluid tube disposed within the tube-receiving sleeve to heat fluid flowing through the fluid tube.

10. The surgical system according to claim 9, wherein the heat exchanger includes at least one heat pipe.

11. The surgical system according to claim 10, wherein a first heat pipe of the at least one heat pipes is disposed within the outer housing and wherein a second heat pipe of the at least one heat pipes is disposed along an exterior of the outer housing.

12. The surgical system according to claim 9, further comprising:
a fluid source configured to supply the fluid to the fluid tube; and
a fluid delivery device configured to receive the fluid from the fluid tube, wherein a temperature of the fluid at the fluid delivery device is greater than a temperature of the fluid at the fluid source.

13. The surgical system according to claim 12, wherein the fluid delivery device is an endoscope.

14. The surgical system according to claim 13, wherein the fluid delivery device is a hysteroscope.

15. The surgical system according to claim 9, wherein a portion of the heat exchanger directly contacts at least one of the at least one waste heat-generating electronic components.

16. The surgical system according to claim 9, wherein the at least one waste heat-generating electronic component includes at least one of: a touch-screen display assembly, a motor control assembly, a power supply, a fluid pump assembly, an identification assembly, or a fluid monitoring assembly.

17. The surgical system according to claim 9, wherein the tube-receiving sleeve defines a C-shaped cross-sectional configuration.

18. A surgical system, comprising:
a fluid source;
a fluid delivery device;
a fluid tube interconnecting the fluid source with the fluid delivery device and configured to enable the flow of fluid from the fluid source to the fluid delivery device; and
a control box, including:
an outer housing;
at least one electronic component disposed within the outer housing and configured to generate waste heat when activated; and a tube-receiving sleeve extending along an exterior of the outer housing, the tube-receiving sleeve disposed in thermal communication with the at least one electronic component and configured to receive the fluid tube therein, wherein, with the fluid tube received within the tube-receiving sleeve and the at least one electronic component activated, waste heat is conducted from the at least one electronic component to the fluid tube to heat the fluid flowing through the fluid tube such that a temperature of the fluid at the fluid delivery device is greater than a temperature of the fluid at the fluid source.

19. The surgical system according to claim 18, wherein at least one heat pipe provides the thermal communication between the tube-receiving sleeve and the at least one electronic component.

20. The surgical system according to claim 19, wherein a first heat pipe of the at least one heat pipes is disposed within the outer housing and wherein a second heat pipe of the at least one heat pipes is disposed along the exterior of the outer housing.

21. The surgical system according to claim 18, wherein the at least one electronic component includes at least one of: a touch-screen display assembly, a motor control assembly, a power supply, a fluid pump assembly, an identification assembly, or a fluid monitoring assembly.

22. The surgical system according to claim 18, wherein the fluid delivery device is an endoscope.

\* \* \* \* \*